United States Patent [19]

Oftring et al.

[11] Patent Number: 5,179,201

[45] Date of Patent: Jan. 12, 1993

[54] ALKYL MONO-AND POLYGLUCOSIDE ETHER CARBOXYLATES, AND THEIR PREPARATION AND USE THEREOF

[75] Inventors: Alfred Oftring, Bad Duerkheim; Elisabeth Kappes, Ludwigshafen; Richard Baur, Mutterstadt; Alexander Kud, Eppelsheim, all of Fed. Rep. of Germany

[73] Assignee: BASF Aktiengesellschaft, Ludwigshafen, Fed. Rep. of Germany

[21] Appl. No.: 695,089

[22] Filed: May 3, 1991

[30] Foreign Application Priority Data

May 16, 1990 [DE] Fed. Rep. of Germany ....... 4015655

[51] Int. Cl.$^5$ .................... C11D 3/37; C11D 3/22
[52] U.S. Cl. .................. 536/41; 252/174.17; 252/174.18
[58] Field of Search ............... 252/174.17, 174.18; 536/4.1

[56] References Cited

U.S. PATENT DOCUMENTS

| | | | |
|---|---|---|---|
| 3,910,880 | 10/1975 | Lamberti | 252/546 |
| 4,488,981 | 12/1984 | Urfer et al. | 252/548 |
| 4,524,009 | 6/1985 | Valenty | 252/89.1 |
| 4,639,325 | 1/1987 | Valenty et al. | 252/89.1 |
| 4,663,071 | 5/1987 | Bush et al. | 252/174.19 |
| 4,804,497 | 2/1989 | Urfer et al. | 252/547 |
| 4,806,275 | 2/1989 | Johnson et al. | 536/4.1 |
| 4,938,888 | 7/1990 | Kiefer et al. | 252/174.17 |
| 5,047,168 | 9/1991 | Broze et al. | 252/174.17 |
| 5,057,311 | 10/1991 | Kamegai et al. | 252/174.17 |
| 5,061,396 | 10/1991 | Lovine et al. | 252/174.17 |
| 5,073,293 | 12/1991 | Deguchi et al. | 252/174.17 |
| 5,077,039 | 12/1991 | Baur et al. | 536/18.6 |

FOREIGN PATENT DOCUMENTS

| | | |
|---|---|---|
| 0075995 | 4/1983 | European Pat. Off. |
| 0258814 | 3/1988 | European Pat. Off. |
| 2439155 | 2/1975 | Fed. Rep. of Germany |
| 2240950 | 3/1975 | France |

OTHER PUBLICATIONS

Phytochemistry Bd, 29, Nr. 2, Oxford UK Seiten 513-515: Hermansson K; Kenne L; Rukunga G M; Samuelsson: "Isolation and Characterization of 2-0-beta. -D-glucopyranosyl-L-malic acid from Synadenium pereskiifolium:" *Seite 513*.

Patent Abstracts of Japan vol. 12, No. 275 (c–516) (3122) Jul. 29, 1988 & JP-A-63 054 390 (Kawaken Fine Chem Co Ltd) Mar. 8, 1988 *Zusammenfassung*.

*Primary Examiner*—Ronald W. Griffin
*Attorney, Agent, or Firm*—Oblon, Spivak, McClelland, Maier & Neustadt

[57] ABSTRACT

Alkyl (poly)glucoside ether carboxylates of the formula

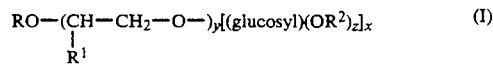

where
R is $C_1$- to $C_{24}$-alkyl, $C_1$- to $C_{24}$-alkylphenyl, hydroxy-$C_2$- to $C_6$-alkyl, hydroxy-$C_1$- to $C_{24}$-alkylphenyl,

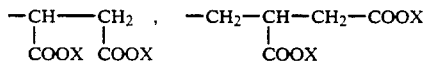

or H,
$R^1$ is H or methyl,
$R^2$ is

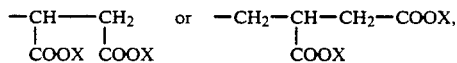

X is a hydrogen, alkali metal, ammonium and/or substituted ammonium equivalent,
x is from 1 to 10, y is from 0 to 10, z is from 1 to 4,
a process for the preparation of the compounds of the formula I and the use of these compounds as an additive to phosphate-free and low-phosphate detergents, are described.

3 Claims, No Drawings

ALKYL MONO-AND POLYGLUCOSIDE ETHER CARBOXYLATES, AND THEIR PREPARATION AND USE THEREOF

The present invention relates to alkyl mono- and polyglucoside ether carboxylates, to their preparation, and to their use as an additive to phosphate-free and low-phosphate detergents.

U.S. Pat. Nos. 4,524,009 and 4,639,325 disclose glycerol ether succinates prepared by reacting glycerol with maleic acid or maleic anhydride in the presence of an alkaline earth metal hydroxide at above 50° C. and at a pH of >10. Each mole of glycerol can undergo an addition reaction with from 1 to 3 mol of maleic acid to form the corresponding glycerol ether succinate. The latter is employed as a substitute for phosphorus- or nitrogen-containing builders in detergents. The glycerol ether carboxylates are biodegradable.

U.S. Pat. No. 4,663,071 discloses builders based on ether carboxylates and obtainable by the addition reaction of 1 or 2 mol of maleic acid with 1 mol of tartaric acid in aqueous solution in the presence of alkaline earth metal and alkali metal ions.

German Laid-Open Application DE-OS 24 39 155 discloses a process for the preparation of builders through the addition reaction, for example, of a monosaccharide or oligosaccharide with an α,β-unsaturated dicarboxyl compound, such as maleic acid, in the presence of an alkaline earth metal hydroxide in aqueous medium, to give builders which are biodegradable.

It is an object of the present invention to provide novel substances.

We have found that this object is achieved by an alkyl mono- or polyglucoside ether carboxylate of the formula $$RO-(CH-CH_2-O)_y[(glucosyl)(OR^2)_z]_x, \quad (I)$$
$$\phantom{RO-(}|$$
$$\phantom{RO-(CH}R^1$$

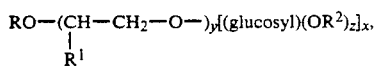

where
R is $C_1$- to $C_{24}$-alkyl, $C_1$- to $C_{24}$-alkylphenyl, hydroxy-$C_2$-to $C_6$-alkyl, hydroxy-$C_1$- to $C_{24}$-alkylphenyl,

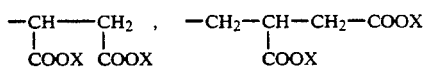

or H,
$R^1$ is H or methyl,
$R^2$ is

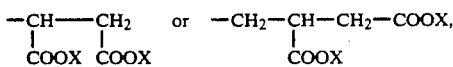

X is a hydrogen, alkali metal, ammonium and/or substituted ammonium equivalent,
x is from 1 to 10,
y is from 0 to 10, and
z is from 1 to 4.

The alkyl mono- or polyglucoside ether carboxylate of the formula I is obtainable by etherifying an alkyl mono- or polyglucoside of the formula

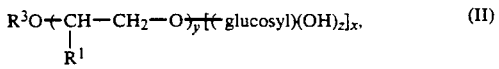

where
$R^3$ is $C_1$- to $C_{24}$-alkyl, $C_1$- to $C_{24}$-alkylphenyl, hydroxy-$C_2$-to $C_6$-alkyl, hydroxy-$C_2$- to $C_{24}$-alkylphenyl or hydrogen,
$R^1$ is H or methyl,
x is from 1 to 10,
y is from 0 to 10, and
z is from 1 to 4,
by reaction with maleic acid and/or itaconic acid in aqueous medium in the presence of 30 mol-% or more of alkaline earth metal ions, based on said dicarboxylic acid, at a pH of from 9 to 13 and at from 50° to 150° C.

The compounds of the formula II are known substances. Alkyl monoglucosides of the formula II are obtainable, for example, by transacetalating a butyl monoglucoside using ethylene glycol or an up to 10-fold ethoxylated $C_1$- to $C_{24}$-alcohol or $C_1$- to $C_{24}$-alkylphenol. Alkyl polyglucosides containing, for example, from 1.3 to 10, preferably up to 3, glucoside units are disclosed, for example, in European Patent 0 075 995. In the formula II, x is preferably from 1 to 3, y is preferably from 0 to 3 and z is preferably from 3 to 4. The compound of the formula II used is preferably hydroxyethyl monoglucoside, a hydroxyethyl polyglucoside containing from 1.3 to 3 glucoside units, an alkyl monoglucoside derived from a $C_{10}$- to $C_{12}$-alcohol or a mixture thereof, an alkyl monoglucoside derived from a from 1- to 10-fold ethoxylated or propoxylated $C_{10}$- to $C_{12}$-alcohol, or an alkyl polyglucoside of a $C_{10}$- to $C_{12}$-alcohol, or a mixture thereof, containing from 1.3 to 3 glucoside units, or a corresponding ethoxylated and/or propoxylated alkyl polyglucoside.

The compounds of the formula II are etherified by reaction with maleic acid, itaconic acid or a derivative of these acids which forms maleic acid or itaconic acid under the reaction conditions. These derivatives include maleic anhydride, itaconic anhydride and the monoesters and diesters of maleic acid and itaconic acid, e.g. monomethyl maleate, dimethyl maleate, diethyl maleate, monomethylitaconate and dimethylitaconate. Etherification using an ester of a dicarboxylic acid gives a reaction medium containing the dicarboxylic acid or a salt thereof and the alcohol on which the ester is based. In aqueous medium, acid anhydrides form the parent dicarboxylic acid or the corresponding salt of the dicarboxylic acid.

The reaction of the alkyl mono- or polyglucoside of the formula II with maleic acid or itaconic acid is carried out in aqueous medium in the presence of alkaline earth metal ions, preferably calcium or barium ions. The alkaline earth metal compound is preferably employed in the form of the oxide or hydroxide. Each mole of the maleic acid or itaconic acid to be reacted requires use of from 0.3 to 1.5 mol, preferably from 0.7 to 1.3 mol, of alkaline earth metal ions. The pH of the reaction medium is from 9 to 13, preferably from 10 to 11.5. An example of a procedure for preparing a compound of the formula I is to add the necessary amount of alkaline earth metal ions to an aqueous solution of the compound of the formula II, and subsequently to add the monoethylenically unsaturated dicarboxyl compound in one or in several portions or continuously. However, it is also possible to add the compound of the formula II to an aqueous solution of the monoethylenically unsaturated dicarboxyl compound and the necessary amount of alkaline earth metal compound or to prepare a mixture of a compound of the formula II and maleic and/or itaconic acid and to initiate the reaction by adding the alkaline earth metal compound and, if desired, another base, such as sodium hydroxide solution, potassium hydroxide solution or a tertiary amine. During the etherification, the amount of base necessary to maintain the pH in the range from 9 to 13 can be added. The necessary amount of base can also be introduced into the reaction system by using, for example, maleic acid or itaconic acid which has been partially (from 20 to 60 mol-%) neutralized by means of an alkali metal base. A preferred procedure involves introducing the compound of the formula II, calcium hydroxide and maleic acid or itaconic acid into the reactor and adding, with thorough mixing, sodium hydroxide solution, potassium hydroxide solution or a tertiary amine during the reaction so that the pH is kept in the range from 9 to 13.

The reaction is carried out in the temperature range from 50° to 150° C., preferably from 60° to 100° C. Reactions carried out at above the boiling point of the reaction mixture involve the use of pressure-tight equipment, e.g. an autoclave, provided with a stirrer. When the reaction is complete, it is in most cases necessary to separate the alkaline earth metal compound employed from the alkyl mono- or polyglucoside ether carboxylate. A preferred procedure for this purpose is to pass carbon dioxide into the reaction mixture, thus precipitating the alkaline earth metal ions from the aqueous solution as the carbonate. The compound of the formula I can subsequently be isolated from the aqueous solution by evaporation or precipitation. If relatively small amounts of by-products are not disturbing, the aqueous reaction solution can be used directly after being substantially freed from alkaline earth metal ions. It is however also possible to purify the alkyl mono- or polyglucoside ether carboxylate by fractional precipitation from the aqueous solution by adding, for example, methanol. Purification is also possible by fractional crystallization from aqueous solution.

The alkyl (poly)glucoside ether carboxylates of the formula I are used as an addition to phosphate-free or low-phosphate detergents and cleaners in an amount of from 0.1 to 20% by weight, based on the particular formulation. For the purposes of the present invention, detergents and cleaners having a reduced phosphate content are taken to mean formulations having a total phosphate content of less than 25% by weight of sodium triphosphate. The compounds of the formula I can be added to the particular detergent or cleaner formulation in the form of granules, a paste, a high-viscosity material, a dispersion or a solution in water. However, they may also be adsorbed onto the surface of fillers, e.g. sodium sulfate, or builders (zeolites or bentonites) or other solid assistants in the detergent formulations.

The composition of detergent formulations may vary widely. The same applies to the composition of cleaner formulations. Detergent and cleaner formulations usually contain surfactants and possibly builders. These data apply both to liquid and powder detergents and cleaners. Examples of detergent formulations which are customary in Europe, in the USA and in Japan are given in tabular form, for example, in Chemical and Engn. News, Volume 67 (1989), 35, and in Ullmanns Encyklopädie der technischen Chemie, Verlag Chemie, Weinheim 1983, 4th Edition, pages 63–160.

Detergent and cleaner formulations are in powder or liquid form. The powder detergents may have different compositions in different regions and for specific applications.

Universal domestic detergents for drum washing machines, as are widely used in Europe, usually contain from 5 to 10% by weight of anionic surfactants, from 1 to 5% by weight of nonionic surfactants, from 1 to 5% by weight of foam regulators, such as silicone oils or soaps, from 0 to 40% by weight of softeners, such as soda or pentasodium triphosphate, which may be partially or completely replaced by the compounds according to the invention, from 0 to 30% by weight of ion exchangers, such as zeolite A, from 2 to 7% by weight of sodium silicates as corrosion inhibitors, from 10 to 30% by weight of bleaches, such as sodium perborate or sodium percarbonate, from 0 to 5% by weight of bleach activators, such as tetraacetylethylenediamine, pentaacetylglucose, hexaacetylsorbitol or acyloxybenzenesulfonate, stabilizers, such as magnesium silicate or ethylenediamine tetraacetate, antigraying agents, such as carboxymethylcellulose, methyl- and hydroxyalkylcelluloses, vinyl acetate-grafted polyglycols, oligomeric and polymeric terephthalic acid/ethylene glycol/polyethylene glycol esters, enzymes, optical whiteners, fragrances, plasticizers, dyes and fillers.

By contrast, heavy duty detergents, which are used in the USA and Japan and neighboring states in tub washing machines, usually contain no bleaches; to make up for this, their content of anionic surfactants is from two to three times as high, they contain more washing alkalis, such as soda and sodium silicates (in general up to 25% by weight), and they naturally also contain no bleach activators and bleach stabilizers. The contents of surfactants and other ingredients may also be considerably higher in detergent concentrates, which are sold containing only a small amount of filler, if any. Detergents for delicate articles, coloreds, woolens and hand washing usually also contain no bleaches and small amounts of alkaline constituents, with a correspondingly increased surfactant content.

Detergents for the commercial sector are formulated for the special conditions of industrial washing (soft water, continuous washing), which allow targeting for the type of material being washed and the type of soiling. Combinations are therefore used in which one constituent predominates or others are entirely missing and can be added separately if needed. For this reason, the surfactants, builders, alkalis and bleaches in these detergents vary within broad limits.

Examples of suitable anionic surfactants for the abovementioned powder detergents are sodium alkylbenzenesulfonates, fatty alcohol sulfates and fatty alcohol polyglycol ether sulfates. Examples of individual compounds of this type are $C_8$- to $C_{12}$-alkylbenzenesulfonates, $C_{12}$- to $C_{16}$-alkanesulfonates, $C_{12}$- to $C_{16}$-alkyl sulfates, $C_{12}$- to $C_{16}$-alkyl sulfosuccinates and sulfated, ethoxylated $C_{12}$- to $C_{16}$-alkanols. Other suitable anionic surfactants are sulfated fatty acid alkanolamines, fatty acid monoglycerides or products of the reaction of from 1 to 4 mol of ethylene oxide with primary or secondary fatty alcohols or alkylphenols. Further suitable anionic surfactants are fatty acid esters or fatty acid amides of hydroxy- or aminocarboxylic acids or -sulfonic acids, for example fatty acid sarcosides, glycolates, lactates, taurides and isethionates. The anionic surfactants may be in the form of sodium, potassium or ammonium salts or as soluble salts of organic bases, such as mono-, di- or triethanolamine or other substituted amines. The anionic surfactants also include the conventional soaps, i.e. the alkali metal salts of natural fatty acids.

Examples of nonionic surfactants are products of the addition reaction of from 3 to 40 mol, preferably from 4 to 20 mol, of ethylene oxide with 1 mol of fatty alcohol, alkylphenol, fatty acid, fatty amine, fatty acid amide or alkanesulfonamide. Particularly important addition products are those of from 5 to 16 mol of ethylene oxide with coconut or tallow fatty alcohols, oleyl alcohol or synthetic alcohols having from 8 to 18, preferably from 12 to 18, carbon atoms, and with mono- or dialkylphenols having from 6 to 14 carbon atoms in the alkyl radicals. Besides these water-soluble nonionics, however, there is also interest in water-insoluble or sparingly water-soluble polyglycol ethers containing from 1 to 4 ethylene glycol ether radicals in the molecule, in particular if they are employed together with water-soluble, nonionic or anionic surfactants.

Other suitable nonionic surfactants are water-soluble products, containing from 20 to 250 ethylene glycol ether groups and from 10 to 100 propylene glycol ether groups, of the addition reaction of ethylene oxide with polypropylene glycol ether, alkylenediaminopolypropylene glycol and alkylpolypropylene glycols having from 1 to 10 carbon atoms in the alkyl chain in which the polypropylene glycol ether chain functions as a hydrophobic radical.

Nonionic surfactants of the amine oxide or sulfoxide type can also be used.

The foaming power of the surfactants can be increased or reduced by combining them with suitable types of surfactant. A reduction can also be achieved by adding non-surfactant organic substances.

A further important constituent in detergent formulations is the encrustation inhibitor, which is, for example, a homopolymer of acrylic acid, methacrylic acid or maleic acid or a copolymer, e.g. of maleic acid and acrylic acid, maleic acid and methacrylic acid or a) acrylic acid and/or methacrylic acid with b) acrylate, methacrylate, vinyl ester, allyl ester, itaconate, itaconic acid, methylenemalonic acid, methylenemalonate, crotonic acid or crotonate. Copolymers of olefins and $C_1$-to $C_4$-alkyl vinyl ethers are also suitable. The molecular weight of the homopolymer or copolymer is from 1,000 to 100,000. The encrustation inhibitor is used in detergents in an amount of from 0.5 to 10% by weight, in unneutralized form, as an alkali metal or ammonium salt or in partially neutralized form, for example with from 40 to 60% of the carboxyl groups neutralized.

Further constituents of detergents may also be monomeric, oligomeric or polymeric phosphonates, ether sulfonates based on unsaturated fatty alcohols, e.g. oleyl alcohol ethoxylate butyl ether, and the alkali metal salts thereof. These substances may be characterized, for example, by the formula $RO(CH_2CH_2O)_2$—$C_4H_8$—$SO_3Na$ where n is from 5 to 40 and R is oleyl.

The above-described alkyl (poly)glycerol ether carboxylates of the formula I can also be used as an additive for liquid detergents, which contain liquid or solid surfactants which are soluble or at least dispersible in the formulation. Suitable surfactants here are products which are also employed in powder detergents, as well as liquid polyalkylene oxides and polyalkoxylated compounds. If the copolymers are not directly miscible with the other constituents of the formulation, homogeneous mixtures can be prepared using small amounts of solubilizers, e.g. water, or a water-miscible organic solvent, e.g. isopropanol, methanol, ethanol, glycol, diethylene glycol or triethylene glycol or corresponding propylene glycols. The amount of surfactant in the liquid detergents is from 4 to 50% by weight, based on the entire formulation, since the proportions of the constituents can also vary within broad limits in liquid detergents, depending on the characteristics of the regional market or the application.

The liquid detergents can contain water in amounts of from 10 to 60% by weight, preferably from 20 to 50% by weight. However, they may also be water-free.

Water-free liquid detergents can also contain peroxo compounds for bleaching in suspended or dispersed form. Examples of specific peroxo compounds are sodium perborate, peroxocarboxylic acids and polymers containing some peroxo-containing groups. The liquid detergents may also contain hydrotropes, which, for the purposes of the invention, are compounds such as 1,2-propanediol, cumenesulfonate and toluenesulfonate. If compounds of this type are employed to modify the liquid detergents, their amount, based on the total weight of the detergents, is from 2 to 5% by weight. In many cases, addition of complexing agents has also proven advantageous for modifying powder and liquid detergents. Examples of complexing agents are ethylenediaminetetraacetic acid, nitrilotriacetate and isoserinediacetic acid, and phosphonates, such as aminotrismethylenephosphonic acid, hydroxyethanediphosphonic acid, ethylenediaminetetraethylenephosphonic acid and salts thereof. Complexing agents are employed in amounts of from 0 to 10% by weight, based on the detergents. The detergents may also contain citrates, diethanolamine, triethanolamine, opacifiers, optical whiteners, enzymes, perfume oils and dyes. If used for modifying liquid detergents, these substances together are present in amounts of up to 5% by weight. The detergents are preferably phosphate-free, but may also contain phosphates, e.g. pentasodium triphosphate and/or tetrapotassium pyrophosphate. If phosphates are employed, the proportion of phosphate in the overall formulation of the detergent is up to 25% by weight.

The alkyl (poly)glucoside ether carboxylates are also suitable as an additive in the aftertreatment of textile goods containing synthetic fibers, e.g. for producing soil release effects. For this purpose, they are added to the final rinse of a washing machine cycle, addition being possible either together with the fabric softener which is usually used at this point or, if a softener is not desired, alone instead of the softener. The amount used is from 0.01 to 0.3 g/l of washing liquor. The use of a compound of the formula I in the final rinse bath of a washing machine cycle has the advantage that the washing in the next wash cycle is soiled much less by detached dirt particles present in the washing liquor than if the antigraying agent is not added in the preceding wash.

The compounds of the formula I according to the invention can also cause synergistic effects with other known detergent additives (e.g. encrustation inhibitors, antigraying agents, clay dispersifiers and substances which increase the primary wash action, color transfer inhibitors, bleach activators) in powder and liquid detergents (phosphate-containing and phosphate-free); these synergistic effects can increase not only the antigraying action, but also the effect of the other detergent additive. The alkyl (poly)glucoside ether carboxylates are particularly suitable for removing particulate dirt, e.g. clay. They are biodegradable. It is noteworthy that $C_8$- to $C_{18}$-alkyl (poly)glucoside ether carboxylates of the formula I where $y=0$ and the corresponding alkoxylated compounds where $y=2$ to 10 and $R^1=H$ simultaneously have surfactant and builder properties.

In the examples, parts and percentages are by weight. The degree of glucosidation x in the formula I was determined by liquid chromatography (HPLC).

EXAMPLES

EXAMPLE 1

90 g of a hydroxyethyl polyglucoside having a degree of glucosidation x of 1.3 were dissolved in 700 ml of water in a reactor equipped with stirrer and reflux condenser. The hydroxyethyl polyglucoside was prepared by the procedure given in Tenside Detergents, Volume 10, Issue 1 (1973) page 2. 119 g (1.6 mol) of calcium hydroxide are then added, and the reaction mixture is heated to 60° C. As soon as this temperature has been reached, 223 g (1.9 mol) of maleic acid are added in portions over the course of 1 hour and the pH of the reaction mixture is also kept in the range from 11 to 11.5 by adding a total of 80 g of 50% strength sodium hydroxide solution. After addition of the maleic acid and sodium hydroxide solution, the reaction mixture is warmed at 80° C. fur a further 6 hours. A total of 75 g of carbon dioxide are then passed in at from 60° to 70° C., the pH being kept at 10 by adding 50% strength aqueous sodium hydroxide solution. The calcium carbonate is then filtered off and washed with 200 ml of water, giving a 35% strength aqueous solution of the sodium salt of hydroxyethyl polyglucoside ether succinate of the formula I where $$R = -CH-CH_2,$$
$$\quad\quad\; |\quad\quad |$$
$$\quad\; COOX\; COOX$$

$R^1=H$,
$y=1$,
$x=1.3$, and
$z \approx 3.1$.

The 35% strength aqueous solution contains, as minor components, sodium salts of maleic acid (1.3%) and fumaric acid (3.1%) and sodium carbonate (1.9%).

EXAMPLE 2

Example 1 was repeated, but employing calcium hydroxide in an amount of 96.2 g (1.3 mol) and maleic acid in an amount of 174 g (1.5 mol). A 35% strength aqueous solution containing, as byproducts, sodium maleate (1.0%), sodium fumarate (2.2%) and sodium carbonate (1.9%), was obtained, In formula I, $z \approx 2.3$.

EXAMPLE 3

Example 1 was repeated, but employing maleic acid in an amount of 139 g (1.2 mol) and calcium hydroxide in an amount of 81 g (1.1 mol). Work-up of the reaction mixture gave a 32% strength aqueous solution containing 0.9% of sodium maleate, 1.5% of sodium fumarate and 2% of sodium carbonate as minor components. In the formula I, z is then $\approx 1.7$.

EXAMPLE 4

Example 1 was repeated, but 160 g of a 70% strength aqueous solution of an alkyl polyglucoside based on a $C_{10}$–$C_{12}$-alcohol and having a degree of glucosidation x of 2.2 with 174 g (1.5 mol) of maleic acid and 111 g (1.5 mol) of calcium hydroxide. Work-up gave a 40% strength aqueous solution of an alkyl polyglucoside ether succinate sodium salt of the formula I where $R=C_{10}/C_{12}$-alkyl,
$y=0$,
$z\approx 2.8$,
$x=2.2$, and

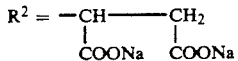

The aqueous solution contained 2.8% of sodium maleate, 3.2% of sodium fumarate and 1.1% of sodium carbonate as minor components.

USE EXAMPLES

The compounds according to the invention are particularly suitable in detergents for removing particulate dirt from fabric surfaces. This property of polyelectrolytes can be determined quantitatively, for example, using clay dispersion.

The stabilization of the dispersion produced after lifting the particles from the fabric surface is an important task of these polyelectrolytes. The stabilizing effect of anionic dispersants is due to adsorption of dispersant molecules on the solid surface, with an increase in surface charge and repulsion energy. Other parameters having an effect on the stability of the dispersion are, inter alia, stearic effects, temperature, pH and electrolyte concentration.

The clay dispersion test (CD test) described below can be used to provide simple assessment of the dispersibility of various polyelectrolytes. CD test The model of particulate dirt used is finely ground china clay SPS 151. 1 g of clay is vigorously dispersed in 98 ml of water for 10 minutes in a measuring cylinder (100 ml) with addition of 1 ml of a 0.1% strength sodium salt solution of the polyelectrolyte. Immediately after stirring, a 2.5 ml sample is taken from the center of the cylinder, diluted to 25 ml using water, and the turbidity of the dispersion is determined using a turbidimeter. After leaving the dispersion to stand for 30 or 60 minutes, further samples are taken and the turbidity determined as above. The turbidity of the dispersion is given in NTU (nephelometric turbidity units). The less settling occurs in the dispersion during storage, the higher the measured turbidity values and the more stable the dispersion.

A second physical parameter determined is the dispersion constant $\tau$, which describes the course of sedimentation with time. Since sedimentation can be described approximately by a monoexponential time law, $\tau$ gives the time for the turbidity to fall to 1/e of the initial value at time $t=0$.

The polyelectrolytes tested were the alkyl polyglucoside ether sodium succinates prepared in Examples 1 to 4. The results obtained are given in the table below:

TABLE

| Example No. | Alkyl polyglucoside ether succinate of Example | Clay dispersion test turbidity after storage | | | Dispersion constant |
|---|---|---|---|---|---|
| | | imediately | 30 min | 60 min | |
| 5 | 1 | 790 | 600 | 560 | 253.7 |

| Example No. | Alkyl polyglucoside ether succinate of Example | Clay dispersion test turbidity after storage | | | Dispersion constant |
|---|---|---|---|---|---|
| | | imediately | 30 min | 60 min | |
| 6 | 2 | 700 | 620 | 530 | 220.3 |
| 7 | 3 | 780 | 650 | 500 | 141.2 |
| 8 | 4 | 670 | 400 | 300 | 76.2 |
| Comparative Example no additive | | 600 | 37 | 33 | 41.4 |

The turbidity values are given in NTU (nephelometric turbidity units).

The alkyl polyglucoside ether succinates from Examples 1 to 4 have a dispersion capacity for clay which is significantly better than that of the comparative example with higher turbidity values (better dispersion) and dispersion constants (higher stability of the dispersion).

We claim:

1. An alkyl mono- or polyglucoside ether carboxylate of the formula $$RO-(CH-CH_2-O-)_y[(glucosyl)(OR^2)_z]_x, \quad (I)$$
$$\underset{R^1}{|}$$

where

R is $C_1$- to $C_{24}$-alkyl, $C_1$- to $C_{24}$-alkylphenyl, hydroxy-$C_2$-to $C_6$-alkyl, hydroxy-$C_1$- to $C_{24}$-alkylphenyl,

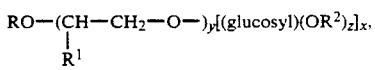

or H, $R^1$ is H or methyl, $R^2$ is

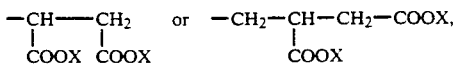

X is a hydrogen, alkali metal, ammonium and/or substituted ammonium equivalent, x is from 1 to 10, y is from 0 to 10, and z is from 1 to 4.

2. A process for the preparation of an alkyl mono- or polyglucoside ether carboxylate of the formula I as claimed in claim 1, which comprises ehterifying an alkyl mono- or polyglucoside of the formula $$R^3O+CH-CH_2-O)_y[(glucosyl)(OH)_2]_x, \quad (II)$$
$$\underset{R^1}{|}$$

where $R^3$ is $C_1$- or $C_{24}$-alkyl, $C_1$- to $C_{24}$-alkylphenyl, hydroxy-$C_2$-to $C_6$-alkyl, hydroxy-$C_2$- to $C_{24}$-alkylphenyl or hydrogen, $R^1$ is H or methyl, x is from 1 to 10, y is from 0 to 10, and z is from 1 to 4, by reaction with maleic acid and/or itaconic acid in aqueous medium in the presence of 30 mol-% or more of alkaline earth metal ions, based on said dicarboxylic acid, at a pH of from 9 to 13 and at from 50° to 150° C.

3. A phosphate-free, low-phosphate or cleaning composition, comprising:

from 0.1 to 20 wt % of the alkyl mono-or polyglucoside ether carboxylate of claim 1 in combination with the remaining constituents of said phosphate-free, low-phosphate or cleaning composition.

* * * * *